US011553984B2

(12) United States Patent
Meglan et al.

(10) Patent No.: US 11,553,984 B2
(45) Date of Patent: Jan. 17, 2023

(54) ROBOTIC SURGICAL SYSTEM WITH AN EMBEDDED IMAGER

(71) Applicant: Covidien LP, Mansfield, MA (US)

(72) Inventors: Dwight Meglan, Westwood, MA (US); Kashif Ikram, Zurich (CH)

(73) Assignees: Covidien LP, Mansfield, MA (US); Covidien AG, Neuhausen am Rheinfall (CH)

(*) Notice: Subject to any disclaimer, the term of this patent is extended or adjusted under 35 U.S.C. 154(b) by 1077 days.

(21) Appl. No.: 16/305,685

(22) PCT Filed: Jun. 2, 2017

(86) PCT No.: PCT/US2017/035582
§ 371 (c)(1),
(2) Date: Nov. 29, 2018

(87) PCT Pub. No.: WO2017/210500
PCT Pub. Date: Dec. 7, 2017

(65) Prior Publication Data
US 2020/0323608 A1    Oct. 15, 2020

Related U.S. Application Data

(60) Provisional application No. 62/345,168, filed on Jun. 3, 2016.

(51) Int. Cl.
*A61B 34/30* (2016.01)
*A61B 90/00* (2016.01)
(Continued)

(52) U.S. Cl.
CPC .............. *A61B 90/37* (2016.02); *A61B 34/37* (2016.02); *A61B 34/70* (2016.02); *A61B 2090/367* (2016.02); *A61B 2090/376* (2016.02)

(58) Field of Classification Search
CPC . A61B 19/201; A61B 19/203; A61B 19/5244; A61B 34/00; A61B 34/30;
(Continued)

(56) References Cited

U.S. PATENT DOCUMENTS 4,894,855 A    1/1990 Kresse
6,132,368 A    10/2000 Cooper
(Continued)

FOREIGN PATENT DOCUMENTS

CN          1406117 A      3/2003
DE    102013221032 A1     4/2015
(Continued)

OTHER PUBLICATIONS

Extended European Search Report dated Jan. 13, 2020 corresponding to counterpart Patent Application EP 17807530.5.
(Continued)

*Primary Examiner* — Vi X Nguyen
(74) *Attorney, Agent, or Firm* — Carter, DeLuca & Farrell, LLP

(57) ABSTRACT

The present disclosure is directed to a robotic surgical system and a corresponding method. The system includes at least one robot arm and a radiation source coupled to the robot arm. The system also includes a surgical table having a digital imaging receiver configured to output an electrical signal based on radiation received from the radiation source. A controller having a processor and a memory is configured to receive the electrical signal and generate an initial image of a patient on the surgical table based on the electrical signal. The controller transforms the initial image to a transformed image based on an orientation of the radiation source.

23 Claims, 4 Drawing Sheets

(51) Int. Cl.
*A61B 34/37* (2016.01)
*A61B 34/00* (2016.01)

(58) Field of Classification Search
CPC ......... A61B 34/37; A61B 34/70; A61B 90/00; A61B 90/37
See application file for complete search history.

(56) References Cited

U.S. PATENT DOCUMENTS

| | | | |
|---|---|---|---|
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,545,914 B2 | 6/2009 | Kito et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco et al. | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez et al. | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |
| 8,600,551 B2 | 12/2013 | Itkowitz et al. | |
| 8,608,773 B2 | 12/2013 | Tierney et al. | |
| 8,620,473 B2 | 12/2013 | Diolaiti et al. | |
| 8,624,537 B2 | 1/2014 | Nowlin et al. | |
| 8,634,957 B2 | 1/2014 | Toth et al. | |
| 8,638,056 B2 | 1/2014 | Goldberg et al. | |
| 8,638,057 B2 | 1/2014 | Goldberg et al. | |
| 8,644,988 B2 | 2/2014 | Prisco et al. | |
| 8,666,544 B2 | 3/2014 | Moll et al. | |
| 8,668,638 B2 | 3/2014 | Donhowe et al. | |
| 8,746,252 B2 | 6/2014 | McGrogan et al. | |
| 8,749,189 B2 | 6/2014 | Nowlin et al. | |

(56) References Cited

U.S. PATENT DOCUMENTS

| | | |
|---|---|---|
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,452 B2 | 9/2015 | Scott et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,861,328 B2 | 1/2018 | Kang et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |

(56) References Cited

U.S. PATENT DOCUMENTS

| | | | |
|---|---|---|---|
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 2011/0015521 | A1 | 1/2011 | Faul |
| 2012/0157819 | A1 | 6/2012 | Jerebko et al. |
| 2014/0107477 | A1* | 4/2014 | Adler .................. A61B 6/12 600/426 |
| 2014/0247918 | A1 | 9/2014 | Kang et al. |
| 2014/0343416 | A1 | 11/2014 | Panescu et al. |
| 2015/0005622 | A1 | 1/2015 | Zhao et al. |

FOREIGN PATENT DOCUMENTS

| | | | |
|---|---|---|---|
| EP | 2774541 | A1 | 9/2014 |
| JP | 4129572 | B2 | 8/2008 |

OTHER PUBLICATIONS

Chinese First Office Action dated Oct. 30, 2020 corresponding to counterpart Patent Application CN 201780031784.6.
Chinese Second Office Action dated Jun. 23, 2021 corresponding to counterpart Patent Application CN 201780031784.6.
International Search Report and Written Opinion of corresponding counterpart Int'l Appln. No. PCT/US17/035582 dated Sep. 8, 2017.

* cited by examiner

ROBOTIC SURGICAL SYSTEM WITH AN EMBEDDED IMAGER

CROSS-REFERENCE TO RELATED APPLICATIONS

This application is a U.S. National Stage Application filed under 35 U.S.C. § 371(a) of International Patent Application Serial No. PCT/US2017/035582, filed Jun. 2, 2017, which claims the benefit of and priority to U.S. Provisional Patent Application Ser. No. 62/345,168, filed Jun. 3, 2016, the entire disclosure of which is incorporated by reference herein.

BACKGROUND

Robotic surgical systems such as teleoperative systems are used to perform minimally invasive surgical procedures that offer many benefits over traditional open surgery techniques, including less pain, shorter hospital stays, quicker return to normal activities, minimal scarring, reduced recovery time, and less injury to tissue.

Robotic surgical systems can have a number of robotic arms that move attached instruments or tools, such as an image capturing device, a grasper, a stapler, an electrosurgical instrument, etc., in response to movement of input devices by a surgeon viewing images captured by the image capturing device of a surgical site. During a surgical procedure, each of the tools may be inserted through an opening, e.g., a laparoscopic port, into the patient and positioned to manipulate tissue at a surgical site. The openings are placed about the patient's body so that the surgical instruments may be used to cooperatively perform the surgical procedure and the image capturing device may view the surgical site.

During the surgical procedure, radiographic imaging may be required to see the status of a patient's internal anatomical structure as well as the location of any surgical tools located therein. The radiographic imaging is performed by a c-arm style fluoroscope that is brought into the operating room or is a dedicated fluoroscope installed within the operating room. The robotic surgical system may have to be disconnected from the patient and moved out of the way in order to position the fluoroscope around the patient to obtain the radiographic images. The disconnecting, movement, and reconnecting of the robotic surgical system will delay the surgical procedure. As a result of this delay, radiographic images may not be fully utilized as a safety monitoring step or to monitor progress of the surgical procedure.

Accordingly, there is a need for obtaining radiographic images without moving the surgical robotic surgical system.

SUMMARY

In an aspect of the present disclosure, a robotic surgical system is provided. The robotic surgical system includes at least one robot arm and a radiation source removably coupled to the robot arm. The system also includes a surgical table having a digital imaging receiver configured to output an electrical signal based on radiation received from the radiation source. A controller having a processor and a memory is configured to receive the electrical signal and generate an initial image of a patient on the surgical table based on the electrical signal. The controller transforms the initial image to a transformed image based on an orientation of the radiation source relative to the digital imaging receiver.

In embodiments, the controller determines a pose of the radiation source relative to the digital imaging receiver. The pose may include an angle between an imaging axis defined by the radiation source and an axis extending perpendicular to a plane defined by the digital imaging receiver. The pose may include a position of the radiation source relative to the digital imaging receiver.

The controller may transform the initial image to the transformed image based on the angle.

In some embodiments, the initial image may be an angled view (e.g., non-perpendicular) of the patient along an imaging axis of the radiation source.

In some embodiments, the controller may execute a movement plan to generate a 3D reconstruction of a patient. The movement plan may cause the controller to move the radiation source a plurality of times. The controller may generate a plurality of initial images, wherein each initial image corresponds to each time the radiation source is moved. The plurality of initial images may be transformed into a plurality of slices that are used to generate the 3D reconstruction.

In another aspect of the present disclosure, a method for imaging a patient using a robotic surgical system is provided. The method includes emitting radiation from a radiation source, receiving radiation from the radiation source using a digital imaging receiver included in a surgical table, and converting the received radiation into an electrical signal. The electrical signal is converted into an initial image which is transformed into a transformed image based on a pose of the radiation source relative to the digital image receiver.

In some embodiments, the method also includes determining the pose of the radiation source relative to the digital image receiver from a position of the radiation source and an angle between an imaging axis defined by the radiation source and a line perpendicular to a plane defined by the digital image receiver. The initial image is transformed into the transformed image based on the pose.

In some embodiments, the initial image may be an angled view of the patient.

In some embodiments, a movement plan is executed to generate a 3D reconstruction of a patient. The movement plan may cause the radiation source to move a plurality of times. A plurality of initial images would be generated, wherein each initial image corresponds to each time the radiation source is moved. The plurality of initial images may be transformed into a plurality of slices that are used to generate the 3D reconstruction.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Fluoroscopic images may be obtained without the use of traditional C-arm style fluoroscopes. The present disclosure is directed to systems and methods for obtaining fluoroscopic images using a robotic surgical system. In the systems described herein, a radiation source is incorporated into an end effector attached to an arm of the robotic surgical system. A receiver can incorporated into the surgical table or place on the surgical table. The receiver is configured to receive x-rays emitted by the radiation source. The received x-rays are converted into an image with an angled perspective which is thereafter transformed into an image with a perpendicular perspective relative to the patient.

By placing the radiation source as an end effector on the robotic arm and the receiver on the operating table, a radiograph may be produced without having to move the surgical robot out of the way of a separate imaging device, e.g., c-arm style fluoroscope or dedicated fluoroscope. By knowing the angle of an orientation of the end effector relative to a plane defined by the surface of the operating table, the obtained images may be corrected to produce an appropriate image, i.e., a perpendicular perspective of the patient.

Figure 1:
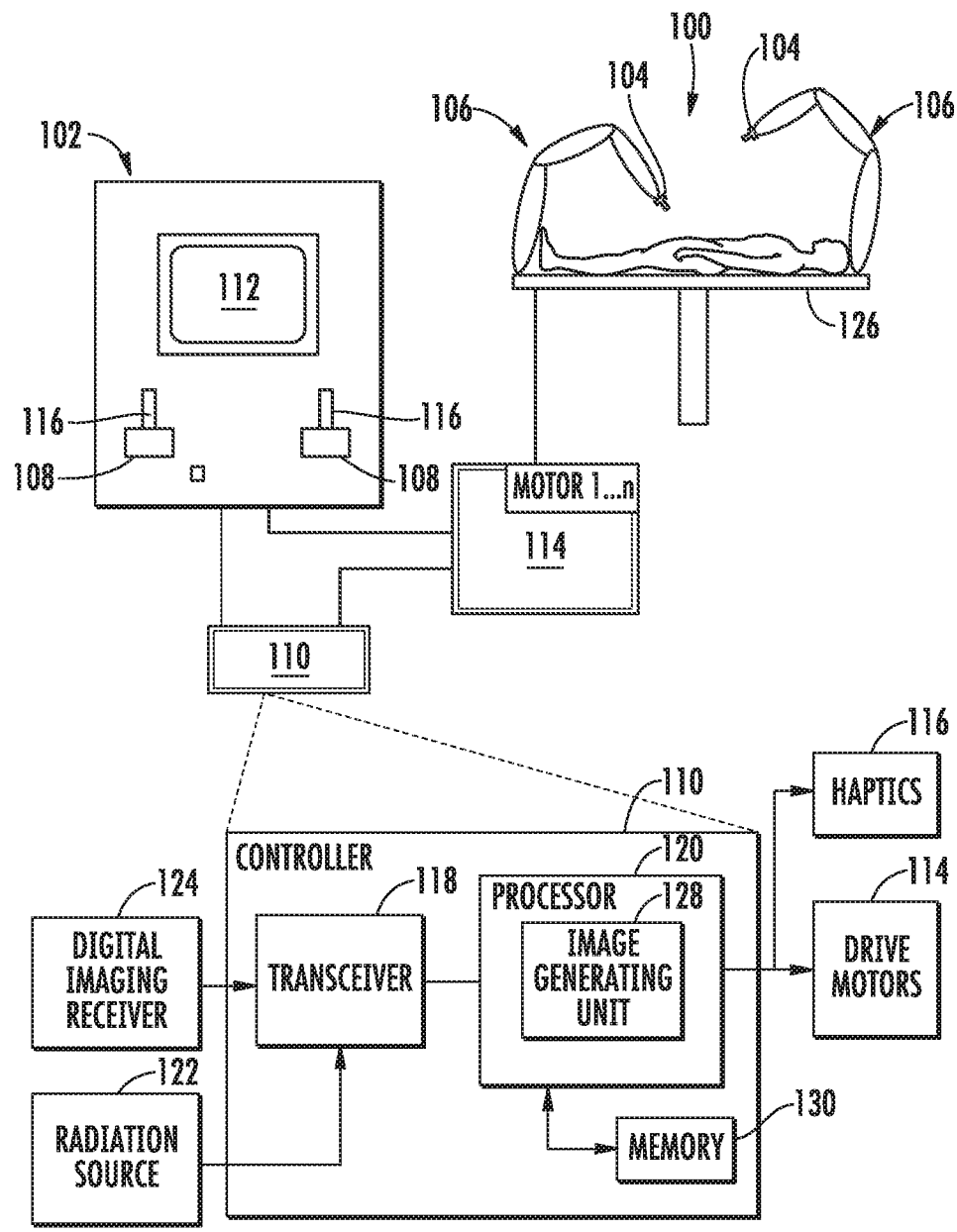
FIG. 1 is a schematic illustration of a user interface and a robotic system of a robotic surgical system in accordance with the present disclosure.

Turning to FIG. 1, a robotic surgical system 100 may be employed with one or more consoles 102 that are next to the operating theater or located in a remote location. In this instance, one team of clinicians or nurses may prep the patient for surgery and configure the robotic surgical system 100 with one or more end effectors 104 while another clinician (or group of clinicians) remotely controls the instruments via the robotic surgical system 100. As can be appreciated, a highly skilled clinician may perform multiple operations in multiple locations without leaving his/her remote console which can be both economically advantageous and a benefit to the patient or a series of patients.

The robotic arms 106 of the surgical system 100 are typically coupled to a pair of master handles 108 by a controller 110. Controller 110 may be integrated with the console 102 or provided as a standalone device within the operating theater. The handles 106 can be moved by the clinician to produce a corresponding movement of the working ends of any type of end effector 104 (e.g., probes, mechanical or electrosurgical end effectors, graspers, knifes, scissors, staplers, etc.) attached to the robotic arms 106. For example, end effector 104 may be a probe that includes an image capture device.

The console 102 includes a display device 112 which is configured to display two-dimensional or three-dimensional images. The display device 112 displays the images of the surgical site which may include data captured by end effector 104 positioned on the ends 114 of the arms 106 and/or include data captured by imaging devices that are positioned about the surgical theater (e.g., an imaging device positioned within the surgical site, an imaging device positioned adjacent the patient, imaging device positioned at a distal end of an imaging arm). The imaging devices may capture visual images, infra-red images, ultrasound images, X-ray images, thermal images, and/or any other known real-time images of the surgical site. The imaging devices transmit captured imaging data to the controller 110 which creates the images of the surgical site in real-time from the imaging data and transmits the images to the display device 112 for display.

The movement of the master handles 108 may be scaled so that the working ends have a corresponding movement that is different, smaller or larger, than the movement performed by the operating hands of the clinician. The scale factor or gearing ratio may be adjustable so that the operator can control the resolution of the working ends of the end effector 104.

During operation of the surgical system 100, the master handles 108 are operated by a clinician to produce a corresponding movement of the robotic arms 106 and/or end effector 104. The master handles 108 provide a signal to the controller 110 which then provides a corresponding signal to one or more drive motors 114. The one or more drive motors 114 are coupled to the robotic arms 106 in order to move the robotic arms 106 and/or end effector 104.

The master handles 108 may include various haptics 116 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 116 provide the clinician with enhanced tactile feedback simulating actual operating conditions. The haptics 116 may include vibratory motors, electroactive polymers, piezoelectric devices, electrostatic devices, subsonic audio wave surface actuation devices, reverse-electrovibration, or any other device capable of providing a tactile feedback to a user. The master handles 108 may also include a variety of different actuators (not shown) for delicate tissue manipulation or treatment further enhancing the clinician's ability to mimic actual operating conditions.

The controller 110 includes a transceiver 118 and a processor 120. Transceiver 118 receives a signal from a radiation source 122 disposed on end effector 104 indicating a position and orientation of the radiation source 122 and a signal from a digital imaging receiver (DIR) 124 disposed on or in the operating table 126, which will be described in more detail below. In some embodiments, the processor 120 may determine the position and orientation of the radiation source 122. The signals from radiation source 122 and/or DIR 124 may be transmitted to transceiver 118 via any conventional wired or wireless methods. Transceiver 118 provides the signal to an image generating unit 128 in processor 120 which generates an image based on the position and orientation of the radiation source 122 and the DIR 124. A memory 130 may store an algorithm used to perform the image generation.

Figure 2:
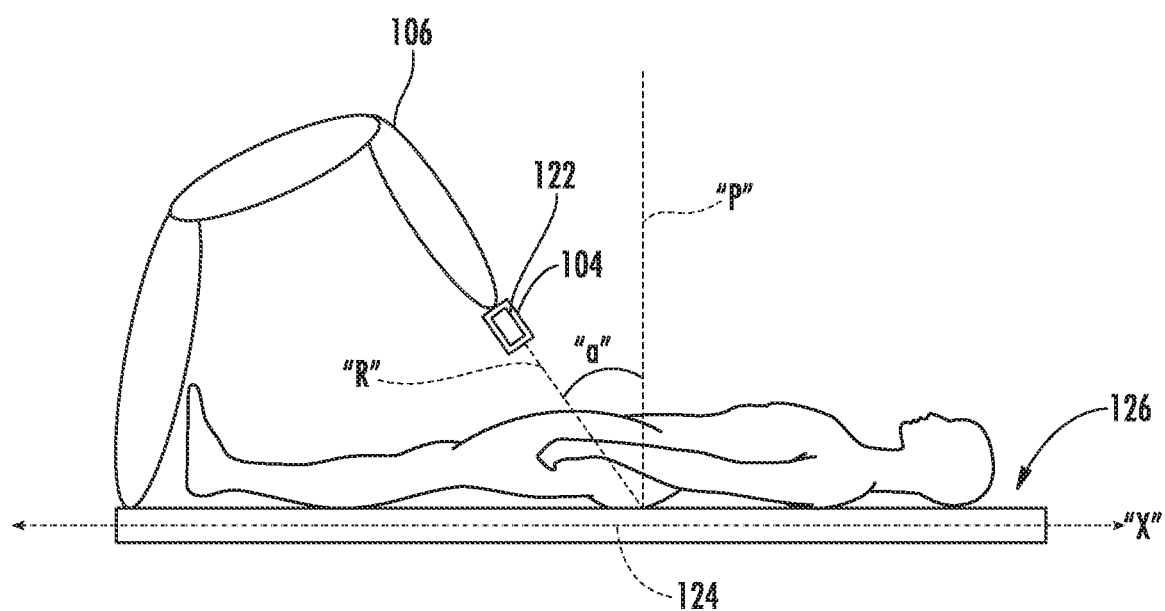
FIG. 2 is a schematic illustration of an imaging system in accordance with the present disclosure.

Turning to FIG. 2, while making reference to FIG. 1, a clinician may attach an end effector 104 including a radiation source 122 to one of the robotic arms 106. The radiation source 122 emits x-rays toward the patient. As the x-rays pass through the patient, the x-rays are attenuated by different amounts as they pass through, having some energy absorbed, or deflect off of various tissues in the patient. The attenuated x-rays are received by the DIR 124 which converts the received x-rays into electrical signals that are provided to the image generating unit 128. The image generating unit converts the electrical signals into an initial image which represents an angled view of the patient.

Once the initial image is generated, the image generating unit 128 uses a pose including the position and the orientation of the radiation source 122 to perform an affine transformation in which the initial image is transformed into a transformed image that would be displayed on display 112. It will be appreciated that the initial image may be a skewed image that is at least keystoned into the transformed image. The perpendicular view presents a view perpendicular the imaging axis "R".

It is contemplated that the transformed image could be a view perpendicular to the patient such that the displayed view is a top plan view perpendicular to a longitudinal axis of the patient. For example, as shown in FIG. 2, the orientation of the radiation source is represented by the angle "a". Angle "a" is the angle between an imaging axis "R" extending through the radiation source 122 and a line "P" perpendicular to the plane "X" of the operating table 126. Based on the angle "a", the image generating unit could perform a transformation of the initial image to the top plan displayed image.

Figure 3:
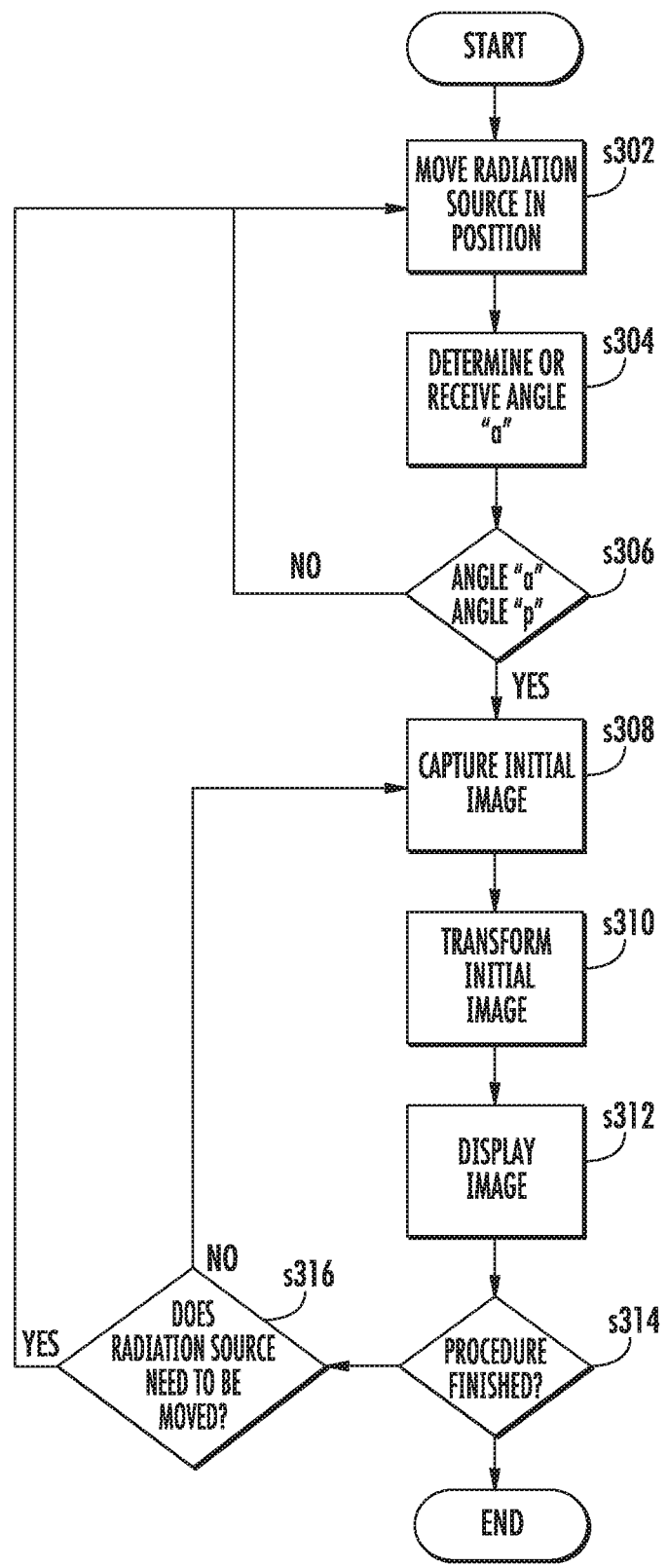
FIG. 3 is a flowchart depicting operation of the imaging system of the present disclosure.

FIG. 3 is a flow chart depicting operation of the imaging system in accordance with embodiments of the present disclosure. FIG. 3 will be described below in conjunction with FIGS. 1 and 2. As shown in FIG. 3, the radiation source 122 is moved into position in step s302. Once in position, the processor 120 determines or receives the pose of the radiation source 122, including the position and the orientation of the radiation source 122, to determine the angle "a" in step s304. In step s306, the processor 120 determines if angle "a" is less than a predetermined angle "p". If angle "a" is not less than predetermined angle "p", the resulting transformed image may not work well or at all. If the angle "a" is not less than the angle "p", the process returns to step s302 where the radiation source is moved. For example, if the misalignment of the predetermined angle "p" and the imaging axis "R" is large, the keystone transformation may create a crude image as a result of large pixilation at one end of the image. If the angle "a" is less than the angle "p", the process proceeds to step s308, where the initial image is generated based on the x-rays received by the DIR 124. The initial image is then transformed in step s310 by the image generating unit 128 to generate a transformed image. The transformed image is then displayed on display 112 in step s312. In step s314, a user may decide to end the procedure or continue the procedure. If the procedure is continued, the user may then determine if the radiation source 122 needs to be moved in step s316. If the radiation source does not need to be moved, the process returns to step s308. If the radiation source needs to be moved, the process returns to step s302.

Figure 4:
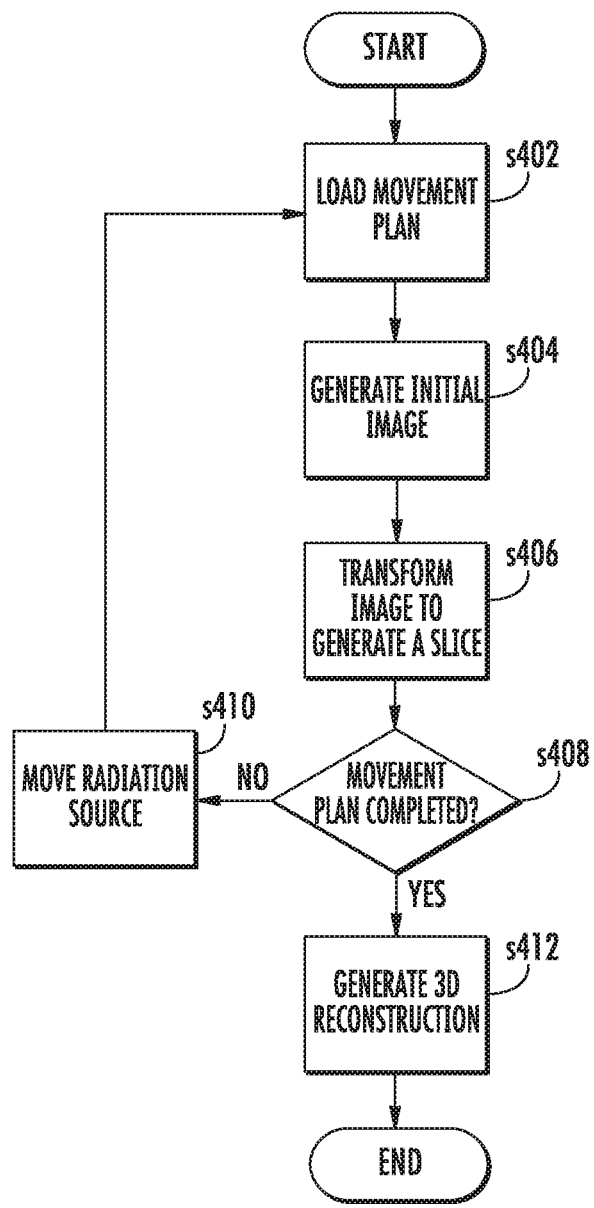
FIG. 4 is a flowchart depicting another operation of the imaging system of the present disclosure.

In some embodiments, the radiation source 122 may be moved according to a movement plan stored in the memory 130. FIG. 4, which will be discussed in conjunction with FIGS. 1 and 2, depicts a method for generating a 3D reconstruction of a patient. As shown in FIG. 4, a movement plan is executed by controller 110 (i.e., the movement plan is loaded from memory 130 to be executed by processor 120) in step s402. In step s404, the controller 110 generates an initial image by controlling the radiation source 122 to emit x-rays and receiving an electrical signal from DIR 124 based on x-rays received from the radiation source 122. The controller then transforms the initial image to an image slice based on the orientation of the radiation source 122 in step s406. For example, if the imaging axis "R" is perpendicular to the centerline of the patient, the image slice is an image of the patient parallel to a transverse plane of the patient. However, it is contemplated that the imaging axis "R" can be disposed at any angle relative to the patient. In step s408, the controller 110 determines whether the movement plan is completed. If the movement plan is not completed, the controller 110 moves the radiation source 122 in step s410 and then proceeds to step s404. If the movement plan is completed, the controller 110 uses the plurality of slices generated by the controller 110 to generate a 3D reconstruction of the patient in step s412.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A user may refer to a surgeon or any medical professional, such as a doctor, nurse, technician, medical assistant, or the like performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A robotic surgical system comprising:
   at least one robot arm;
   a radiation source removably coupled to the robot arm;
   a surgical table having a digital imaging receiver configured to output an electrical signal based on radiation received from the radiation source; and
   a controller having a processor and a memory, the controller is configured to receive the electrical signal and generate an initial image of a patient on the surgical table based on the electrical signal, wherein the controller is configured to:
      transform the initial image to a transformed image based on an orientation of the radiation source relative to the digital imaging receiver;
      execute a movement plan to generate a 3D reconstruction of the patient, wherein the movement plan causes the controller to move the radiation source a plurality of times;
      generate a plurality of initial images, wherein each initial image corresponds to each time the radiation source is moved; and
      transform the plurality of initial images to a plurality of slices.

2. The robotic surgical system of claim 1, wherein the controller determines a pose of the radiation source relative to the digital imaging receiver.

3. The robotic surgical system of claim 2, wherein the pose includes an angle between an imaging axis defined by the radiation source and an axis extending perpendicular to a plane defined by the digital imaging receiver.

4. The robotic surgical system of claim 3, wherein the pose includes a position of the radiation source relative to the digital imaging receiver.

5. The robotic surgical system of claim 2, wherein the controller transforms the initial image to the transformed image based on the determined pose.

6. The robotic surgical system of claim 1, wherein the initial image is an angled view of the patient along an imaging axis of the radiation source.

7. The robotic surgical system of claim 1, wherein the 3D reconstruction is based on the plurality of slices.

8. A robotic surgical system comprising:
   a radiation source supported on a robot arm;
   a surgical table having a digital imaging receiver configured to output an electrical signal based on radiation received from the radiation source; and
   a controller having a processor and a memory, the controller is configured to receive the electrical signal and generate an initial image of a patient on the surgical table based on the electrical signal, wherein the controller is configured to:
      transforms the initial image to a transformed image based on an orientation of the radiation source relative to the digital imaging receiver;
      executes a movement plan to generate a 3D reconstruction of the patient, wherein the movement plan causes the controller to move the robot arm to reposition the radiation source a plurality of times;
      generates a plurality of initial images, wherein each initial image corresponds to each time the radiation source is moved; and
      transforms the plurality of initial images to a plurality of slices.

9. The robotic surgical system of claim 8, wherein the controller determines a pose of the radiation source relative to the digital imaging receiver.

10. The robotic surgical system of claim 9, wherein the pose includes an angle between an imaging axis defined by the radiation source and an axis extending perpendicular to a plane defined by the digital imaging receiver.

11. The robotic surgical system of claim 10, wherein the pose includes a position of the radiation source relative to the digital imaging receiver.

12. The robotic surgical system of claim 9, wherein the controller transforms the initial image to the transformed image based on the determined pose.

13. The robotic surgical system of claim 8, wherein the initial image is an angled view of the patient along an imaging axis of the radiation source.

14. The robotic surgical system of claim 8, wherein the 3D reconstruction is based on the plurality of slices.

15. The robotic surgical system of claim 8, further comprising a repositionable robot arm supporting the radiation source.

16. A robotic surgical system comprising:
   a robot arm configured for selective repositioning;
   a radiation source coupled to the robot arm;
   a surgical table having a digital imaging receiver configured to output an electrical signal based on radiation received from the radiation source; and
   a controller having a processor and a memory, the controller is configured to receive the electrical signal and generate an initial image of a patient disposed on the surgical table based on the electrical signal, wherein the controller is configured to:
      transform the initial image to a transformed image based on an orientation of the radiation source relative to the digital imaging receiver;
      execute a movement plan to generate a 3D reconstruction of the patient, wherein the movement plan causes the controller to reposition the robot arm to move the radiation source a plurality of times;
      generate a plurality of initial images, wherein each initial image corresponds to each time the robot arm is repositioned to move the radiation source; and
      transform the plurality of initial images to a plurality of slices.

17. The robotic surgical system of claim 16, wherein the controller determines a pose of the radiation source relative to the digital imaging receiver.

18. The robotic surgical system of claim 17, wherein the pose includes an angle between an imaging axis defined by the radiation source and an axis extending perpendicular to a plane defined by the digital imaging receiver.

19. The robotic surgical system of claim 18, wherein the pose includes a position of the radiation source relative to the digital imaging receiver.

20. The robotic surgical system of claim 17, wherein the controller transforms the initial image to the transformed image based on the determined pose.

21. The robotic surgical system of claim 16, wherein the initial image is an angled view of the patient along an imaging axis of the radiation source.

22. The robotic surgical system of claim 16, wherein the 3D reconstruction is based on the plurality of slices.

23. The robotic surgical system of claim 16, wherein the radiation source is selectively connected to the robot arm.

* * * * *